United States Patent [19]

Nebashi et al.

[11] Patent Number: 4,992,198

[45] Date of Patent: Feb. 12, 1991

[54] DETERGENT COMPOSITION CONTAINING CLATHRATE GRANULES OF A PERFUME-CLATHRATE COMPOUND

[75] Inventors: Tutomu Nebashi; Shinichi Yabe; Fumio Sai, all of Tochigi; Yu Izumi; Takashi Fujieda, both of Chiba, all of Japan

[73] Assignee: Kao Corporation, Tokyo, Japan

[21] Appl. No.: 297,842

[22] Filed: Jan. 13, 1989

[30] Foreign Application Priority Data

Jan. 19, 1988 [JP] Japan .................................... 63-9163
Jan. 29, 1988 [JP] Japan .................................. 63-19254

[51] Int. Cl.$^5$ .......................... C11D 3/50; A61K 7/46

[52] U.S. Cl. .................................. 252/174.11; 512/2; 512/3; 512/4; 252/174.13

[58] Field of Search .................................. 512/2, 3, 4; 252/174.11, 174.13

[56] References Cited

U.S. PATENT DOCUMENTS 4,576,737 3/1986 Johnson .......................... 252/174.11
4,639,326 1/1987 Czempik et al. ...................... 252/91

FOREIGN PATENT DOCUMENTS 3020269 8/1982 Fed. Rep. of Germany ........................ 252/174.11

OTHER PUBLICATIONS

Koch J., *Stabilization and Controlled Release of Perfume in Detergents,* Int. Symp. on Cyclodextrins, 1981, pp. 487, 490, and 495.

*Primary Examiner*—Robert A. Wax
*Assistant Examiner*—Eric Steffe
*Attorney, Agent, or Firm*—Flynn, Thiel, Boutell & Tanis

[57] ABSTRACT

A high density-having, granular, concentrated detergent composition comprises a detergent component(s) and clathrate granules of a perfume-clathrate compound comprising a perfume and a compound having a clathration capability. The clathrate granules have an average size of 100 to 1500 micrometers.

12 Claims, No Drawings

DETERGENT COMPOSITION CONTAINING CLATHRATE GRANULES OF A PERFUME-CLATHRATE COMPOUND

The present invention relates to a granulation product of a perfume and a powdery detergent composition containing the same.

PRIOR ART

A perfume is generally a liquid (although, as a matter of course there are also solid perfumes such as camphor) and used for various applications. One of the applications is as an ingredient of a powdery detergent for clothing and is used for masking the odor of the raw material and giving comfort to the users during the use of the detergent. Although a liquid perfume can easily be added to a liquid detergent, no satisfactory method has been proposed for the addition of a liquid perfume to a powdery detergent. In general, the liquid perfume is sprayed on a powdery detergent. Alternatively, the liquid perfume is added to the powdery detergent in the form of the so-called master powder prepared by preliminarily mixing the liquid perfume with part of the ingredients of the detergent and powdering and compressing the resulting mixture.

Home washing is usually repeated 2 to 3 times per washing liquid. When a powdery detergent for clothing containing a perfume added thereto is used for the washing, the perfume component is volatilized upon pouring of the detergent, and its odor is weakened in a few minutes, so that its masking effect disappears. In some cases, the mere addition of a perfume brings about relatively favorable fragrance in the first washing or relatively easily provides masking because less dirty clothing is first washed. However, in the second and third washings, the odor emitted from the clothing is strong because very dirty clothing is washed, so that no sufficient masking is attained through addition of the perfume by a usual method.

In order to make the fragrance persistent, an attempt has been made to add a powdery perfume prepared by including a perfume in an including compound, such as cyclodextrin, to a powdery detergent (see West German Patent No. 3020269). Although the use of such a powdery perfume inclusion compound beings about a slight improvement in the persistency of the fragrance, this expedient is insufficient for masking the odor emitted from the clothing in the above-described repeated washing.

In recent years, there is an ever-increasing demand for a high-density, powdery and concentrated detergent from the viewpoint of saving of resource, transportability of the detergent, easiness of carrying the detergent by housewives and storage space.

High-density powdery detergents are disclosed in Japanese Patent Laid-Open Nos. 61511/1973, 36508/1978, 132093/1983, etc. All the above documents relate to an improvement in the general composition, process or solubility of the high-density powdery detergent, and none of them are concerned with the fragrance of the high-density powdery detergent.

It is a common practice to perfume a detergent with a given amount of a perfume, and this expedient is necessary for enhancing the value of the goods through masking of an odor accompanying the raw material of the detergent and imparting of a proper fragrance to a washing liquid and clothings.

However, the high-density, granular and concentrated detergent (wherein the term "high density" is intended to mean a bulk specific gravity of at least 0.5 $g.cm^3$) has a disadvantage over the conventional low-density detergent (bulk specific gravity: usually about 0.3 $g/cm^3$) that since the high-density, granular and concentrated detergent has a high content of an active ingredient, such as a surfactant, for the purpose of reducing the amount (weight and volume) of use of the detergent per washing (e.g., from 40 g/30 l to 25 g/30l) through an increase in the density, the amount of the perfume component relative to the washing liquid and the washing is decreased according to the amount of the use, so that the fragrance of the washing liquid and the fragrance remaining in the washed clothings are too weak.

Increasing the percentage perfuming is easily considered as an expedient for compensating for this drawback. However, this expedient brings about an excessively strong odor of the detergent powder per se which unfavorably gives an uncomfortable feeling to the consumers.

The perfume has, as an osmophore group, a functional group such as a hydroxyl, aldehyde, ester, ketone, nitro, amino, ether or cyano group, or a double bond, and, in general, many of them easily brings about decomposition, denaturation, or polymerization of an alkaline or zeolite detergent such as a heavy duty powdery detergent for clothing. For this reason, an increase in the percentage perfuming is unfavorable because it increases the tendency of causing the decomposition and denaturation of the perfume.

SUMMARY OF THE INVENTION

The present inventors have made extensive and intensive studies with a view to solving the above-described problems and, as a result, have found that the problems can be solved by mixing a powdery detergent with a granulated perfume prepared by powdering a perfume with an including compound and granulating the powdered perfume, which has led to the completion of the present invention.

In the invention, a perfume-clatharate compound is used and it is called also the perfume-inclusion compound in the instant specification.

The invention provides a high density, granular, concentrated detergent composition which comprises a detergent component(s) and clathrate granules of a perfume-clathrate compound comprising a perfume and a compound having a clathration capability.

It is preferable that the clathrate granules have an average size of 100 to 1500 micrometers. More specifically, the clathrate granules have such a size distribution that 5 wt. % or less of the granules have a size of less than 100 micrometers and 5 wt. % or less of the granules have a size of more than 1500 micrometers. The invention further provides a composition comprising 10 to 60 wt. % of a surfactant, 30 to 80 wt. % of a builder and 0.1 to 5 wt. % of the clathrate granules.

The invention moreover relates to the above shown chlathrate granules.

The invention also provides a process for preparing the detergent composition and a method of perfuming a high-density, granular and concentrated detergent comprising perfuming a high-density, granular and concentrated detergent with a perfume composed of a liquid perfume component having high stability and low volatility in an alkaline or zeolite system and a liquid perfume component having low stability and high volatility in an alkaline or zeolite system, characterized in that a liquid perfume component having high stability and low volatility in an alkaline or zeolite system is sprayed on a high-density, granular and concentrated detergent material or preliminarily mixed with part of said detergent component and added to said detergent in the form of a master powder prepared by powdering the resultant mixture; or a perfume component having low stability and high volatility an alkaline or zeolite system is included in a compound having an inclusion capability, granulated to prepare a granulation product of a perfume inclusion material and added to said granular detergent.

The invention is characterized by the use of the granules of the perfume-clathrate compound or granulation product of a perfume inclusion powder.

The inclusion compound used in the present invention is most preferably β-cyclodextrin. However, β-cyclodextrin derivatives, such as methylated β-cyclodextrin, α-cyclodextrin, γ-cyclodextrin, etc. may also be used.

Inclusion of a perfume in an inclusion compound followed by powdering may be conducted by a commonly employed method. In general, the inclusion compound of the perfume can be prepared by gradually adding a perfume to a slurry or an aqueous solution of an inclusion compound while stirring the slurry or aqueous solution, collecting a perfume inclusion material by filtration and drying the perfume inclusion material. The perfume and the inclusion compound are used in a molar ratio of 0.8 to 1.2.

The powered perfume is granulated by dry or wet process by making use of a binder. The dry process is one wherein water is not used in combination with the binder, while the wet process is one ,wherein water is used in combination with the binder. The binder is an organic compound having a melting point or a softening point of 40° to 160° C. Examples of the organic compound having a melting point or a softening point of 40° to 160° C. include polyethylene glycol having a molecular weight of 1500 to 20000, a polyethylene glycol alkyl ether having an alkyl group of 8 to 22 carbon atoms, polyethylene glycol alkylphenol ether having an alkyl group of 8 to 22 carbon atoms, an aliphatic acid having an alkyl group of 12 to 37 carbon atoms, and an ethylene oxidepropylene oxide block polymer.

The powdered perfume is mixed with a binder and further, if necessary, an extender, such as Glauber's salt, an physical property improver for a powder, such as silica, and other additives, and the mixture is extruded. The extrudate is granulated by granulation method, rolling granulation method, or the like. In granulating the powdered perfume, it is preferred that the perfume inclusion material powder, the binder, the extender, and the physical property improver for a powder be used in respective amounts of 20 to 80 parts by weight (hereinafter abbreviated to "parts"), 5 to 35 parts, 15 to 50 parts, and 0 to 5 parts, respectively.

The powdered perfume is granulated so as to have an average particle diameter of 100 to 1500 μm, preferably 200 to 1300 μm, more preferably 300 to 1000 μm. It is preferred that the percentage of the particles having a diameter less than 100 μm and exceeding 1500 μm be 5% by weight (hereinafter abbreviated to "%"). The granulation product is generally incorporated in an amount of 0.1 to 5% in a detergent composition such as a high density granular detergent.

The granules of the perfume-clathrate compound or powdery perfume inclusion compound may have an average particle diameter of 100 to 1000 micrometers.

Specifically, a liquid perfume material having high stability and low volatility in an alkaline or zeolite system is sprayed on a high-density, granular and concentrated detergent material or preliminary mixed with part of the detergent component and then added to the detergent in the form of a master powder prepared by powdering the mixture, while a liquid perfume material having low stability and high volatility in an alkaline or zeolite system is granulated after inclusion thereof in a compound having an inclusion capability to form a granulation product of a perfume inclusion powder and then added to a granular detergent.

The perfume material having high stability and low volatility in an alkaline or zeolite system which is generally used in the art is an alcohol, an ester of a secondary or tertiary alcohol, a ketone, or an ether, and specific examples thereof include the following perfumes.

(i) Alcohols: synthetic sandalwood oil, benzyl alcohol, phenylethyl alcohol, styrallyl alcohol, dimethylbenzyl carbinol, etc.

(ii) Ketones: Tentarome, acetophenone, benzophenone, α-damascone, methyl amyl ketone, etc.

(iii) Esters: hedion, hexyl salicylate, isoamyl salicylate, flutate, methyl benzoate, etc.

(iv) Ethers: diphenyl oxide, amyl phenylethyl ether, Cedramber, nerolin yara-yara, anethole, etc.

(v) Others: aldehyde C-14 peach, cumarin, pentalyde, musk ambrette, methyl anisuranylate, etc.

As usual, these perfume materials are sprayed on a granular detergent material or added to the detergent in the form of a master powder prepared by mixing the perfume material with part of the detergent component and powdering the resulting mixture.

Examples of the perfume having low stability and high volatility in an alkaline or zeolite system which have been regarded being unsuitable for an alkaline or zeolite system include the following compounds.

(1) Monoterpene hydrocarbons and their derivatives:

(i) Monoterpene hydrocarbons: limonene, α-pinene β-pinene, terpinolene, myrcene, etc.

(ii) Derivatives:

Alcohols: citronellol, linalool, geraniol, etc.

Ketones: l-menthone, l-carvone, camphor, etc.

Esters: citronellyl acetate, geranyl acetate, teripinyl acetate, etc.

Aldehydes: citral and citranellal.

Others: citronellyl nitrile, geranyl nitrile, eucalyptol, etc.

(2) Aldehydes having 6 to 15 carbon atoms except for compounds described in the above item (1): aldehydes of 8 to 14 carbon atoms, lilal, anisaldehyde, benzaldehyde, α-n-amylcinnamic aldehyde, α-n-hexylcinnamic aldehyde, lillial, heliotropin, cinnamic aldehyde, etc.

(3) Formate or acetates having 5 to 15 carbon atoms except for the compounds described in the above item (1): benzyl formate, phenylethyl formate, anisyl acetate, benzyl acetate, phenylethyl acetate, cinnamyl acetate, p-tert-butylcyclohexyl acetate, isoamyl acetate, cis-3-hexyl acetate, etc.

The granules of the perfume-clathrate compound is introduced in a detergent composition or a high density-having, concentrated detergent composition. The detergent composition may further comprise, in addition to the perfume-clathrate compound, 10 to 60 wt. % of a surfactant, such as a straight-chain alkylbenzenesulfonate, an alkyl sulfate, a polyoxyethylene alkyl ether sulfate, an α-olefinsulfonate, a higher fatty acid salt, or a polyoxyethylene alkyl ether; 30 to 80% of a detergent builder, such as a carbonate, a silicate, a sulfate, a phosphate, or a zeolite; 0.1 to 5% of the above-described powdery perfume inclusion compound; 0 to 30% of a bleaching agent, such as a percarbonate or a perborate; about 2 to 6% in total of the other ingredients, e.g., an anti-redeposition agent such as polyethylene glycol or carboxymethylcellulose, an enzyme such as protease or cellulase, and a fluorescent dye.

In order to obtain a desired fragrance, the perfume is generally added to the detergent in the form of a compound perfume prepared by compounding various perfumes. The granulation product of the powdery inclusion compound of the compound perfume per se can be added to the detergent. However, when volatile perfume ingredients having a vapor pressure of 100 mmHg or less at 25° C. are added as a granulation product of a powdery perfume inclusion compound while hardly volatile ingredients are added to the detergent in a conventional manner, no significant change in the fragrance during repeated washing occurs and excellent persistency of the fragrance can be attained, and further, an economic advantage can be offered because the necessary amount of the including compound can be reduced.

The compound perfume is usually incorporated in an amount of about 0.1 to 0.5% in the detergent. The whole or part of the compound perfume is incorporated in the detergent in the form of a granulation product of a powdery perfume inclusion compound. Although the amount of incorporation of the granulation product of the perfume varies depending upon the perfume content of the granulation product and the compound perfume composition, the granulation product is used in an amount of 0.1 to 5% by weight in the case of a perfume composition commonly used in a detergent for clothing.

The granulation product of a perfume according to the present invention enables an improvement in the persistency of the fragrance when added to a powdery detergent, a shampoo, a bath liquid, etc. Further, since the granulation product of a perfume according to the present invention causes no lowering in the stability for a long period of time even when it is brought into contact with an alkali, the odor emitted from the wash can be sufficiently masked even in the case of repeated washing.

At least one of the above-described perfumes is included in a compound having an inclusion capability, granulated to prepare a perfume inclusion material granule, and incorporated in a high-density granular detergent.

Although there is no particular limitation with respect to the composition of the high-density, granular and concentrated detergent composition according to the present invention, if necessary, the following components may be incorporated in the detergent composition.

(1) Anionic surfactants such as alkylbenzenesulfonates, alkyl or alkenyl ether sulfates, alkyl- or alkenylsulfates, olefin sulfonates, alkane sulfonates, saturated or unsaturated fatty acid salts, α-sulfofatty acid salts or esters, and alkyl or alkenyl ether carbonates (anionic surfactant content: usually 25 to 50%, preferably 30 to 40%).

(2) Polyoxyalkylene alkyl or alkenyl ethers, polyoxyethylenealkyl phenyl ether, higher fatty acid alkanolamides or their alkylene oxide adducts, sucrose fatty acid esters, fatty acid glycerin monoesters, and alkylamine oxides.

(3) Surfactants such as betaine type amphoteric surfactants, sulfonic acid type amphoteric surfactants, phosphate activators, and cationic surfactants.

(4) Alkaline agents such as silicates, carbonates, and sesquicarbonates.

(5) Sequestering agents for divalent metal ions zeolites (aluminosilicates), orthophosphates, pyrophosphates, tripolyphosphates, nitrilotriacetates, ethylenediaminetriacetates, citrates, isocitrates, polyacrylic acid, and polyacetalcarboxylic acid.

(6) Anti-redeposition agents such as polyvinyl alcohol, polyvinyl pyrrolidone, carboxymethyl cellulose, and polyethylene glycol.

(7) Bleaching agents such as sodium percarbonate, sodium perborate, and an adduct of sodium sulfate with hydrogen peroxide.

(8) Enzymes such as protease, esterase, lipase, and cellulase.

(9) Other components usually used for detergent such as caking preventives, bleaching activators, stabilizers for peroxides, antioxidants, fluorescent dyes, bluing agent and photoactive bleaching agents.

There is no particular limitation with respect to the method of preparing the high-density, concentrated and granular detergent. For example, the high-density, concentrated and granular detergent can be prepared, e.g., by a method which comprises adding an alkaline agent and an acid-resistant detergent component to an unneutralized anionic surfactant, neutralizing the mixture, adding zeolite and tripoli or the like, and grinding the mixture, or a method wherein a powdery detergent prepared by spray drying is granulated to increase the bulk density.

The bulk density is at least 0.5 g/cm$^3$, preferably 0.5 to 1.2 g/cm$^3$, more preferably 0.7 to 1.2 g/cm$^3$.

The particle diameter of the high-density, concentrated and granular detergent is preferably 2,000 μm or less, and 3% or less, preferably 1% or less of the particles has a diameter of 125 μm or less.

The present invention enabled the preparation of a high-density granular detergent exhibiting fragrance of the powder, fragrance of the washing liquid and residual fragrance of the clothings, each having a strength substantially equal to that attained by the conventional low-density detergent. Further, the present invention has an advantage that the high-density granular detergent undergoes no change in fragrance note, even when stored for a long period of time. Furthermore, in the present invention, since a perfume which has hitherto been regarded as having low stability or high volatility in an alkaline or zeolite system can also be used without causing any problem, the degree of freedom with respect to the perfuming of a perfume is increased, which makes it possible to provde a fragrance note which has not been attained in the prior art.

EXAMPLES

The present invention will how be described in detail with reference to the following Examples which should not be construed as limiting the scope of the present invention.

Example 1 and Comparative Examples 1 to 5

Low-density detergents and high-density, granular and concentrated detergents having compositions shown in Table 1 were prepared. These detergents are perfumed with perfume compositions shown in Table 2. With respect to the perfumed detergents, fragrance of the powder, fragrance of the washing liquid, residual fragrance of washed clothings, and stability of the perfume were examined and compared. The results are shown in Table 3.

TABLE 1

| | Recipe of detergent (unit of all numerals in the Table is wt %) | |
|---|---|---|
| | composition 1 (for low-density detergent) | composition 2 (for high-density granular and concentrated detergent) |
| LAS | 10 | 16 |
| AOS | 10 | 16 |
| soap | 1.5 | 2.4 |
| nonion | 1.5 | 2.4 |
| zeolite (4A type) | 15 | 24 |
| sodium carbonate | 10 | 16 |
| sodium silicate No. 2 | 5 | 8 |
| sodium sulfate | balance | balance |
| Polyethylene glycol | 2 | 3.2 |
| small amounts of additives | 2 | 3.2 |
| water | 4 | 6.4 |
| total | 100 | 100 |

The ingredients shown in Table 1 are as follows:

LAS: straight-chain sodium alkylbenzenesulfonate (12 to 13 carbon atoms)

AOS: sodium α-olefinsulfonate (16 to 18 carbon atoms)

soap: tallow soap (16 to 18 carbon atoms)

nonion: polyoxyethylene alkyl ether (12 to 13 carbon atoms; $\overline{EO}=10$)

polyethylene glycol: an average molecular weight of about 13,000 small amounts of additives: fluorescent dyes, enzymes, etc.

The amounts of individual ingredients except for sodium sulfate incorporated in Composition 2 are each 1.6 times larger than that of each ingredient incorporated in composition 1 shown in Table 1. That is, composition 2 is the so-called concentrated composition which provides the same concentration of each ingredient as that of each ingredient of composition 1 when used in an amount of 1/1.6 of composition 1.

The composition of a perfume used is shown in Table 2.

TABLE 2

| Composition of perfume | |
|---|---|
| lemon muguet | |
| *phenylethyl alcohol | 20% |
| (1) limonene | 20% |
| (1) citral | 5% |
| (2) Lilial | 10% |
| (2) α-hexylcinnamic aldehyde | 20% |
| (2) Lyral | 15% |
| (3) benzyl acetate | 10% |
| total | 100% |

The method of preparing a low-density detergent and a high-density, granular and concentrated detergent, a method of perfuming the detergent, a method of evaluating fragrance, and stability of fragrance will now be described. The following method of preparing the detergent is only one of the preferred embodiments and not limited to this only.

(1) Method of preparing detergent

A slurry was prepared so as to have a water content of 50% by weight and a composition corresponding to composition 1 shown in Table 1 but not containing ingredients, such as 2% by weight of zeolite and enzyme among small amounts of additives, which provide better results when dry-blended in the later step. The slurry was spray-dried, and the resultant powder was dry-blended with the above-described ingredients of composition 1 which have not been added in the former step to prepare a low-density detergent of composition 1 having a bulk density of 0.30 g/cm$^3$.

Separately, a slurry was prepared so as to have a water content of 50% by weight and a composition corresponding to composition 2 shown in Table 1 but not containing ingredients, such as 10% by weight of zeolite and enzyme among small amounts of additives, which provide better results when dry-blended in the later step. The slurry was spray-dried. The resultant powder was put into a high speed mixer (agitation rolling granulator; a product of Fukae Kogyo K.K.). 5% by weight of zeolite which had been wetted with 1% by weight of water was added thereto, and the powder was disintegrated and granulated. 3% by weight of zeolite was further added, and disintegration and granulation were conducted. The resultant particles were dry-blended with the remaining zeolite, i.e., 2% by weight of zeolite, and small amounts of additives to prepare a high-density, granular and concentrated detergent of composition 2 having a bulk density of 0.75 g/cm$^2$.

(2) Method of perfuming (A) 100 parts of the above-described powdery detergent was sprayed with the above-prepared perfume.

(B) 100 parts of the above-described powdery detergent was sprayed with the perfume ingredient marked with * among the ingredients of the above-prepared perfume, and a perfume inclusion material powder was prepared from the other perfume ingredients by the following method and mixed with the above-perfumed detergent.

(C) 100 parts of the above-described powdery detergent was sprayed with the perfume ingredient marked with * among the ingredients of the above-prepared perfume, and a granulation product of a perfume inclusion material powder was prepared from the other perfume ingredients by the following method and mixed with the above-perfumed detergent.

Evaluation was conducted on the detergents prepared by the above methods.

Preparation of perfume inclusion material powder and granulation product thereof 18.0 g of Celdex N (β-cyclodextrin) manufactured by Nihon Shokuhin Kako Co., Ltd. was added and completely dissolved in 200 ml of hot water of 60° C. 2.5 g of the blended perfume was added thereto, and the mixture was stirred for 3 hr. After addition of the blended perfume, there was observed an inclusion phenomenon through formation of water-insoluble precipitates. The precipitates were collected by filtration and then freeze-dried to prepare 20 g of a perfume inclusion material powder. The inclusion material powder was mixed so as to have the following composition, and the mixture was granulated with an extrusion granulator manufactured by Fuji Paudal Co., Ltd. (Model EXKS-1) to prepare granules. The granules were classified with each of 16- and 32-mesh sieves to obtain the following granules.

| | |
|---|---|
| inclusion material | 50% |
| PEG-6000 | 25% |
| neutral anhydrous Glauber's salt | 25% |
| particle size distribution of granules: | |
| average particle size | 670 μm |
| 1500 μm or more | 1.0% |
| less than 100 μm | 4.0% |

(3) Evaluation of fragrance (i) Evaluation of fragrance of detergent powder

About 50 $cm^3$ of the detergent was placed in a wide-mouthed bottle having a capacity of 100 $cm^3$ and covered with a lid. The strength of the fragrance emitted upon opening of the lid was evaluated by ten trained panelists by the paired comparison method wherein the fragrance of the sample was compared with that of a reference detergent. The reference detergent was prepared by perfuming 100 parts by weight of the low-density detergent having composition 1 with 0.12 part by weight of a perfume by the perfuming method A.

The evaluation criteria are as follows.

| evaluation score | criteria for evaluation |
|---|---|
| 2 | fragrance considerably stronger than that of the reference detergent |
| 1 | fragrance slightly stronger than that of the reference detergent |
| 0 | fragrance having the same strength as that of the reference detergent |
| −1 | fragrance slightly weaker than that of the reference detergent |
| −2 | fragrance considerably weaker than that of the reference detergent |

The results of evaluation was expressed in terms of the sum of the product of the number of panelists who gave each score and the evaluation score. That is, the larger the sum value, the stronger the fragrance.

(ii) Evaluation of fragrance of washing liquid 40 g of the low-density detergent having composition 1 and 25 g of the high-density, granular and concentrated detergent having decomposition 2 were each separately dissolved in 30 l of tap water of 20° C. in a washing machine. Upon dissolution of the detergent, the strength of the fragrance of the washing liquid was evaluated in the same manner as that described in the above-item (i).

(iii) Evaluation of residual fragrance of washed clothing 1 kg of cotton underwear was put in the washing liquid used in the above item (ii), washed for 10 min, and dehydrated for 1 min, rinsed while flowing tap water of 20° C. at a flow rate of 15 l/min for 6 min, dehydrated for 3 min, air-dried overnight within a room, and evaluated with respect to the strength of the residual fragrance in comparison with the fragrance of the cotton underwear similarly treated with the reference detergent in the same manner as that described in the above item (i).

(4) Evaluation of stability of perfume

50 $cm^3$ of the detergent was placed in a wide-mouthed bottle having a capacity of 100 $cm^3$, covered with a lid, stored at −5° C., 30° C., and 40° C. for 20 days, and evaluated with respect to the stability of the perfume by 10 panelists through an organoleptic test.

| | |
|---|---|
| | no change |
| ~Δ | slight change |
| Δ | significant change |

EXAMPLE 2

Granulation products of perfume inclusion compounds were prepared by the following method, and detergents containing said granulation products were subjected to evaluation of the persistency of the odor and stability.

(1) Preparation of granulation products of perfume inclusion compound 18.0 g of Celdex N (β-CD) manufactured by Nippon Shokuhin Kako Co., ltd. was completely dissolved in 200 ml of hot water at 60° C. 2.3 g of a compound perfume described hereinbelow was added thereto, and the mixture was stirred for 3 hr. After the addition of the compound perfume, there was observed an inclusion phenomenon through formation of water-insoluble precipitates. The precipitates were recovered by filtration and then freeze-dried to prepare 20 g of a powdery perfume inclusion compound. The inclusion compound was mixed so as to have the following composition, and the mixture was granulated with an extrusion granulator (Eckpelleter, a product of Fugi Denki K. K.) to prepare granules. The granules thus prepared were classified with a 32-mesh sieve to obtain the following granules:

TABLE 3

| | | reference | Comp. Ex. 1 | Comp. Ex. 2 | Comp. Ex. 3 | Comp. Ex. 4 | Comp. Ex. 5 | Ex. 1 |
|---|---|---|---|---|---|---|---|---|
| composition of detergent | | 1 | 2 | 2 | 2 | 2 | 2 | 2 |
| bulk density (g/$cm^3$) | | 0.30 | 0.75 | 0.75 | 0.75 | 0.75 | 0.75 | 0.75 |
| percentage perfuming* | | 0.12 | 0.12 | 0.15 | 0.19 | 0.12 | 0.15 | 0.19 |
| perfuming method | | A | A | A | A | B | B | C |
| fragrance of powder | | reference | −4 | +9 | +20 | +3 | +5 | +1 |
| fragrance of washing liquid | | reference | −16 | −6 | ±0 | −3 | −1 | −1 |
| residual fragrance of clothing | | reference | −18 | −8 | ±0 | −5 | −2 | ±0 |
| stability of perfume | −5° C. | ~Δ | ~Δ | Δ | Δ | | ~Δ | |
| | 30° C. | Δ | Δ | Δ | Δ | | Δ | |
| | 40° C. | Δ | Δ | Δ | Δ | ~Δ | Δ | |

Note:
*the percentage perfuming is the amount of perfume added in terms of parts by weight based on 100 parts by weight of the detergent.

| | |
|---|---|
| inclusion compound | 50% |
| PEG 6000 | 25% |
| neutral anhydrous Glauber's salt | 25% |
| Particle size distribution of granules: | |
| average particle diameter | 670 μm |
| 1000 μm or more | 1.0% |
| less than 100 μm | 4.0% |
| Compound perfume | |
| terpinolene | 0.5% |
| limonene | 47.5% |
| α-pinene | 5.0% |
| citral | 3.0% |
| eugenol | 2.0% |
| allyl amyl glycolate | 5.0% |
| benzyl acetate | 20.0% |
| phenyl ethyl acetate | 3.0% |
| geranyl acetate | 4.0% |
| linalyl acetate | 10.0% |
| total | 100.0% |

(2) Perfume-containing powdery detergent composition

A high density-having detergent having the following composition was prepared:

| | |
|---|---|
| sodium dodecylbenzenesulfonate | 30.0% |
| Softanol 120 | 3.0% |
| tallow fatty acid sodium soap | 2.8% |
| sodium carbonate | 10.0% |
| sodium silicate No. 2 | 9.5% |
| type 4A zeolite | 23.5% |
| sodium sulfate | the balance |
| polyethylene glycol 6000 | 2.0% |
| carboxymethylcellulose | 1.5% |
| Tinopal CBS (fluorescent dye) | 0.35% |
| water | 4.5% |
| total | 100% |

100 parts of the above-described powdery detergent was either (A) sprayed with 0.2 part of the above-described compound perfume, or (B) mixed with 2 parts of the above-described powdery perfume inclusion compound, or (C) mixed with 4 parts of the above-described granulation product of the powdery inclusion compound, thereby preparing perfume-containing detergents (A), (B), and (C) wherein detergents (B) and (C) have the same perfume content.

(3) Evaluation of persistence of odor

The odor of a washing liquid in each of the first, second, and third washings conducted under the following washing conditions by making use of detergents (A), (B), and (C) was evaluated by four panelists (male 25-year old; male 36-year old; female 36-year old; and female 18-year old), and the average of the scores was determined. The results are shown in Table 4.

washing machine: Ginga manufactured by Toshiba Corporation; 2.2 kg amount of water: 30 l amount of detergent: 25 g clothing: 1 kg

[600 g of cotton undershirts and 400 g of T/C shirts (worn for 3 days); they were taken out each time and newly put in the washing liquid].

washing time: 7 min

TABLE 4

| detergent | 1st washing | 2nd washing | 3rd washing |
|---|---|---|---|
| (A) | 7 | 12 | 12 |
| (B) | 5 | 10 | 12 |
| (C) | 4 | 5 | 8 |

| | |
|---|---|
| Evaluation score: | |
| no offensive odor of wash | 1 |
| weak offensive odor of wash | 2 |
| strong offensive odor of wash | 3 |

The higher the score, the stronger the offensive odor during washing.

(4) Evaluation of stability of perfume

A 100-ml sample bottle was charged with 50 g of each of detergents (A), (B), and (C), hermetically sealed, stored at −5°, 30° and 40° C. for 20 days, and evaluated with respect to the stability of the perfume by the same panelists as those described above. The results are shown in Table 5.

| | |
|---|---|
| | the same as the stability of the detergent stored at −5° C. for 20 days |
| ~Δ | slight change |
| Δ | significant change |

TABLE 5

| detergent | −5° C. | 30° C. | 40° C. |
|---|---|---|---|
| (A) | | Δ | Δ |
| (B) | | ~Δ | ~Δ |
| (C) | | | |

We claim:

1. A high-density, granular, concentrated detergent composition comprising a detergent component(s) and clathrate granules of a perfume clathrated with cyclodextrin or a derivation thereof, said detergent component(s) comprising 25 to 50% by weight of an anionic surfactant and said clathrate granules comprising 20 to 80 parts by weight of a perfume-clathrate powder, 5 to 35 parts by weight of polyethylene glycol binder having a molecular weight of 1,500 to 20,000 and 15 to 50 parts by weight of Glauber's salt.

2. A composition as claimed in claim 1, in which the clathrate granules additionally comprise silica.

3. A composition as claimed in claim 1, in which the granules have an average size of 100 to 1,500 microns.

4. A composition as claimed in claim 1, in which the granules have such a size distribution that 5 wt. % or less have a size of less than 100 microns and 5 wt. % or less of the granules have a size of more than 1,500 microns.

5. A composition as claimed in claim 1, which comprises 10 to 60 wt. % of a surfactant, 30 to 80 wt. % of a builder and 0.1 to 5 wt. % of the clathrate granules.

6. A composition as claimed in claim 1, in which the detergent component(s) comprises 25 to 50% by weight of an anionic surfactant.

7. A clathrate granule comprising 20 to 80 parts by weight of a perfume clathrated with cyclodextrin or a derivation thereof, 5 to 35 parts by weight of a binder and 15 to 50 parts by weight of an extender.

8. A high-density, granular, concentrated detergent composition comprising a detergent component(s) and granules of a perfume clathrated with cyclodextrin or a derivation thereof said detergent component(s) comprising 25 to 50% by weight of an anionic surfactant, said granules comprising 20 to 80 parts by weight of a perfume-clathrate powder, 5 to 35 parts by weight of a binder selected from the group consisting of polyethylene glycol having a molecular weight of 1,500 to 20,000, a polyethylene glycol alkyl ether having an alkyl group of 8 to 22 carbon atoms, a polyethylene glycol alkyl phenol ether having an alkyl group of 8 to 22 carbon atoms, an aliphatic acid having an alkyl group of 12 to 37 carbon atoms and an ethylene oxide-propylene oxide block polymer, and 15 to 50 parts by weight of Glauber's salt.

9. A composition as claimed in claim 8, in which the clathrate granules additionally comprise silica.

10. A composition as claimed in claim 8, which the granules have an average size of 100 to 1500 micrometers.

11. A composition as claimed in claim 8, in which the granules have such a size distribution that 5 wt. % or less of the granules have a size of less than 100 microns and 5 wt. % or less of the granules have a size of more than 1500 microns.

12. A composition as claimed in claim 8, which comprises 10 to 60 wt. % of a surfactant, 30 to 80 wt. % of a builder and 0.1 to 5 wt. % of the clathrate granules.

* * * * *

UNITED STATES PATENT AND TRADEMARK OFFICE
CERTIFICATE OF CORRECTION

PATENT NO. : 4 992 198

DATED : February 12, 1991

INVENTOR(S) : Tutomu NEBASHI et al

It is certified that error appears in the above-identified patent and that said Letters Patent is hereby corrected as shown below:

Column 13, line 1; change "derivation" to ---derivative---.
after "thereof" insert a comma.
line 3; after "said" insert ---clathrate---.

Column 14, line 13; delete "clathrate".

Signed and Sealed this

Twelfth Day of January, 1993

Attest:

DOUGLAS B. COMER

Attesting Officer

*Acting Commissioner of Patents and Trademarks*